United States Patent
Adams

(10) Patent No.: US 9,861,740 B2
(45) Date of Patent: Jan. 9, 2018

(54) COMBINATION LINEAR POTENTIOMETER AND SYRINGE THUMBPRESS DETECTION SENSOR AND RELATED SYSTEMS AND METHODS

(71) Applicant: Smiths Medical ASD, Inc., Rockland, MA (US)

(72) Inventor: Grant Adams, Coon Rapids, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 88 days.

(21) Appl. No.: 14/899,891

(22) PCT Filed: Jun. 26, 2014

(86) PCT No.: PCT/US2014/044306
§ 371 (c)(1),
(2) Date: Dec. 18, 2015

(87) PCT Pub. No.: WO2015/002806
PCT Pub. Date: Jan. 8, 2015

(65) Prior Publication Data
US 2016/0136353 A1    May 19, 2016

Related U.S. Application Data

(60) Provisional application No. 61/842,618, filed on Jul. 3, 2013.

(51) Int. Cl.
*A61M 5/145* (2006.01)

(52) U.S. Cl.
CPC ........ *A61M 5/1452* (2013.01); *A61M 5/1458* (2013.01); *A61M 2205/14* (2013.01); *A61M 2205/332* (2013.01)

(58) Field of Classification Search
CPC .... A61B 6/481; A61B 5/4839; A61M 5/1458; A61M 2205/332; A61M 5/1452;
(Continued)

(56) References Cited

U.S. PATENT DOCUMENTS 4,767,406 A     8/1988  Wadham et al.
4,838,857 A *   6/1989  Strowe ................ A61M 5/1456
                                              128/DIG. 12
(Continued)

FOREIGN PATENT DOCUMENTS

EP      0 388 102 A2    9/1990
EP      1279410 A1      1/2003

OTHER PUBLICATIONS

PCT International Search Report and Written Opinion for PCT/US/2014/044306, dated Oct. 15, 2014, 10 pgs.
(Continued)

*Primary Examiner* — Gerald Landry, II
(74) *Attorney, Agent, or Firm* — Patterson Thuente Pedersen, P.A.

(57) ABSTRACT

A combined detectional and positional sensor for a syringe pump. The sensor can comprise a syringe thumbpress clamp that is pivotable so that an engagement pin deflects a linear membrane potentiometer first circuit thus providing a closed switch for detection of a syringe in the pump and a variable signal return for indication of plunger head position. Embodiments of the sensor can be used in relatively large syringe pumps and in relatively small syringe pumps, for example.

4 Claims, 5 Drawing Sheets

(58) Field of Classification Search
CPC .............. A61M 5/172; A61M 5/14566; A61M 2005/14208; A61M 2202/0007; A61M 5/007
USPC .................. 604/67, 121, 131, 151–155, 208
See application file for complete search history.

(56) References Cited

U.S. PATENT DOCUMENTS

| | | | | |
|---|---|---|---|---|
| 5,254,096 | A * | 10/1993 | Rondelet | A61M 5/1456 417/63 |
| 5,326,416 | A * | 7/1994 | Perrett | B29C 65/7841 156/251 |
| 5,533,981 | A * | 7/1996 | Mandro | A61M 5/1458 604/208 |
| 5,662,612 | A * | 9/1997 | Niehoff | A61M 5/14546 417/15 |
| 7,041,085 | B2 | 5/2006 | Blomquist | |
| 7,742,186 | B2 | 6/2010 | Murakami et al. | |
| 2003/0229311 | A1 * | 12/2003 | G. Morris | A61M 5/1456 604/151 |
| 2004/0024361 | A1 * | 2/2004 | Fago | A61M 5/31525 604/152 |
| 2007/0191770 | A1 * | 8/2007 | Moberg | A61M 5/14566 604/131 |
| 2011/0009812 | A1 * | 1/2011 | Brown | A61B 5/155 604/31 |
| 2011/0097229 | A1 * | 4/2011 | Cauley, III | A61M 5/1454 417/518 |
| 2013/0184676 | A1 * | 7/2013 | Kamen | G06F 19/3406 604/506 |
| 2013/0336814 | A1 * | 12/2013 | Kamen | A61M 5/16859 417/282 |
| 2015/0297832 | A1 | 10/2015 | Blomquist | |

OTHER PUBLICATIONS

Reinhard, K., "Choosing potentiometers for position sensing". Electronicproducts, Oct. 25, 2011, <URL=http://www.electronicproducts.com/Sensors_and_Transducers/Sensors_and_Transducers/Choosing_potentiometers_for_position_sensing.aspx>.
http://www.sensofoil.com/products-solutions/sensofoil/), Sensofoil, Hoffmann + Krippner, Jun. 5, 2013, 2 pages.
http://www.designworldonline.com/membrane-potentionmeters-simplify-position-sensing/#_, "Membrane Potentiometers Simplify Position Sensing" May 12, 2010, Design World Staff, Hoffmann + Krippner, Inc., Jun. 5, 2013, 4 pages.
International Preliminary Report on Patentability, International Application No. PCT/US2014/044306, dated Jan. 14, 2016, 7 pages.
European Search Report for European Application No. 14819901.1 dated Feb. 2, 2017.

* cited by examiner

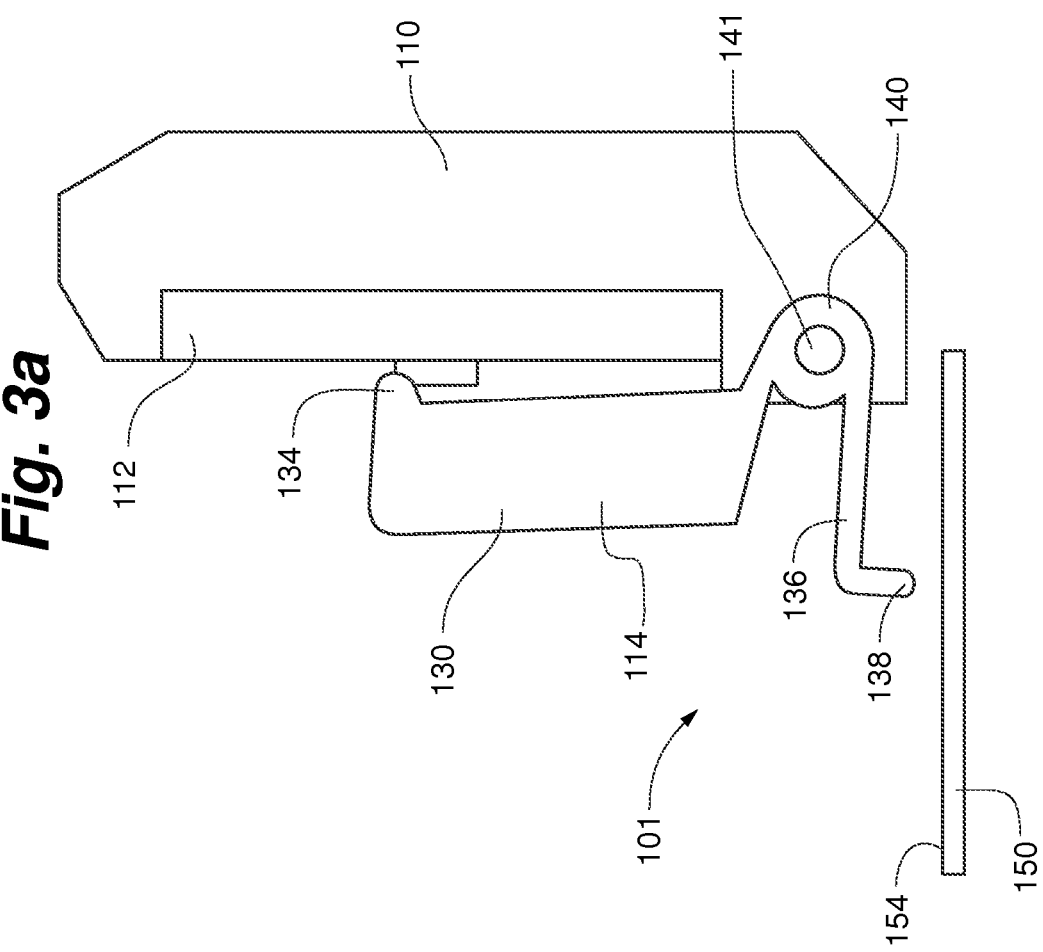

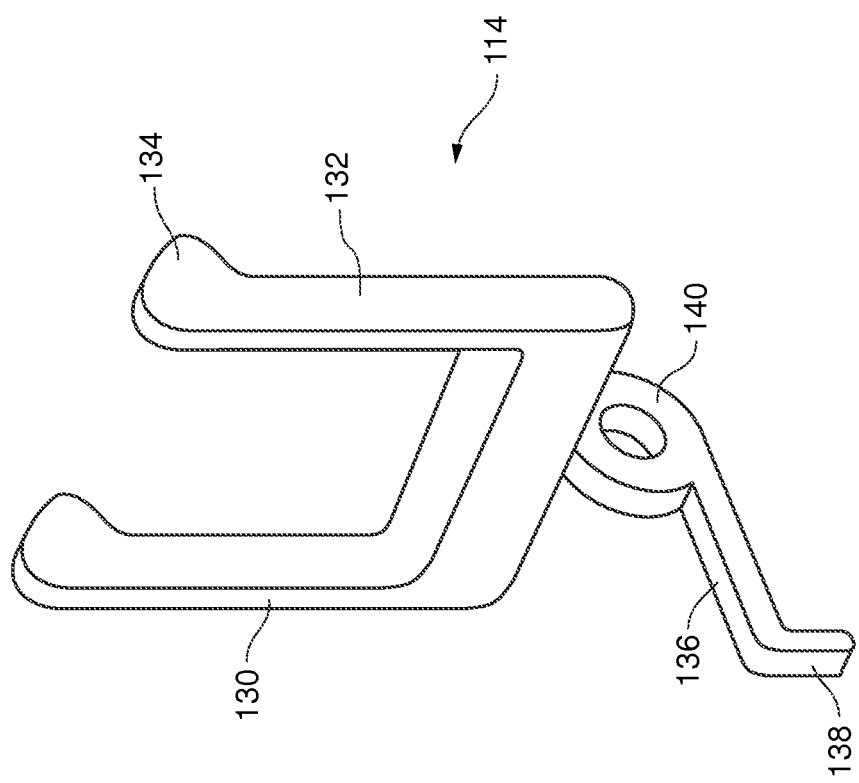

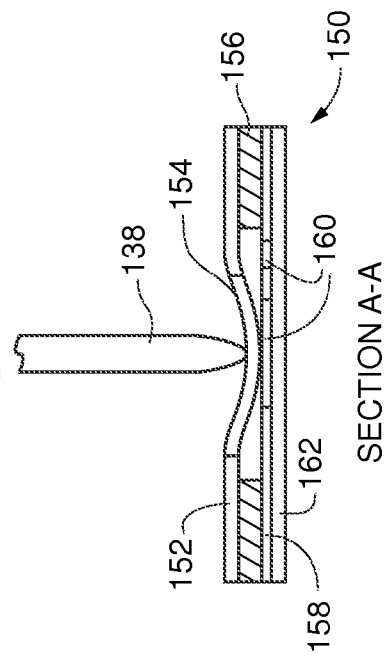
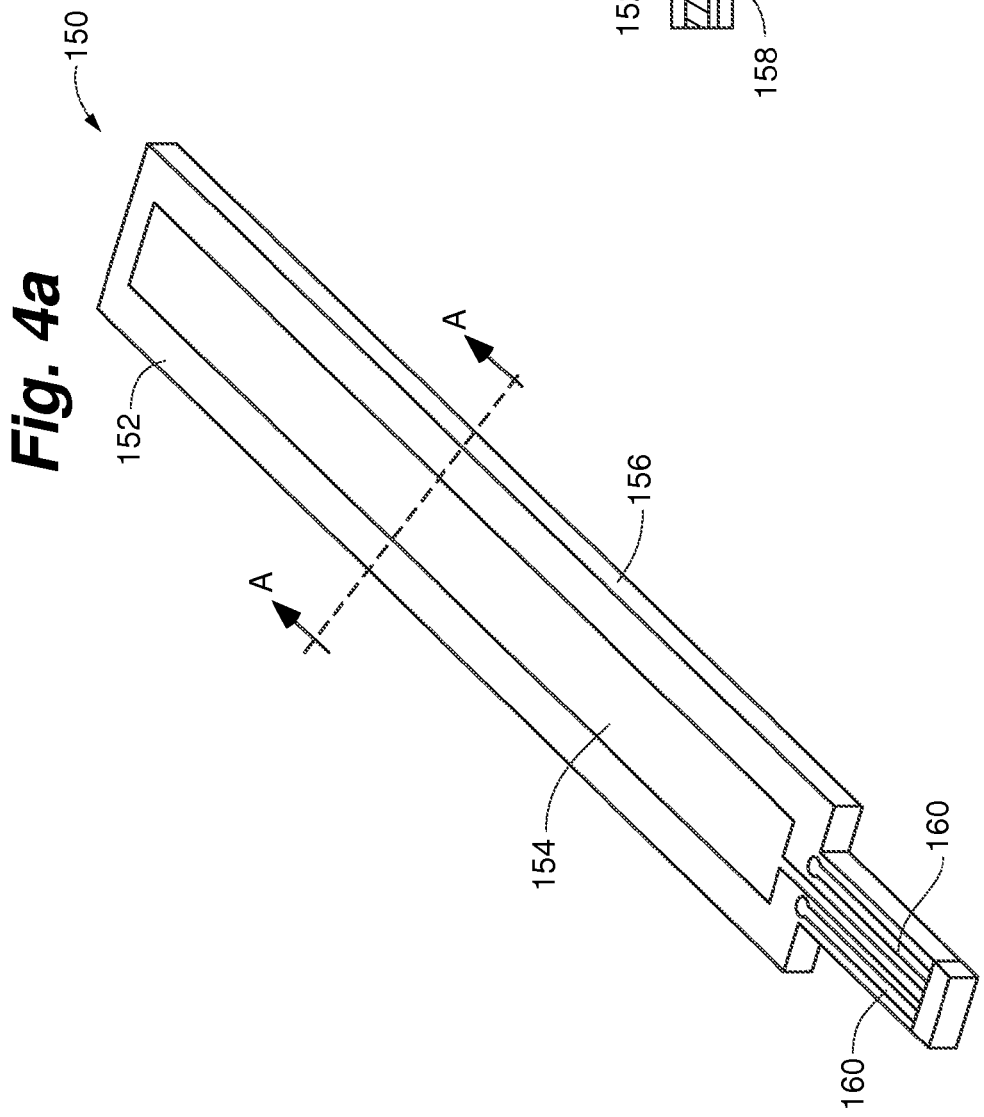

COMBINATION LINEAR POTENTIOMETER AND SYRINGE THUMBPRESS DETECTION SENSOR AND RELATED SYSTEMS AND METHODS

RELATED APPLICATIONS

The present application is a National Phase entry of PCT Application No. PCT/US2014/044306, filed Jun. 26, 2014, which claims the benefit of U.S. Provisional Patent Application No. 61/842,618, filed Jul. 3, 2013, each of which is incorporated herein by reference in its entirety.

TECHNICAL FIELD

Subject matter hereof relates generally to medical devices. More particularly, the subject matter relates to syringe pumps and systems for, and methods of, determining a presence of and correctly locating a syringe thumbpress within the syringe pump and determining a linear position of a plunger head. The subject matter thus relates to a device configured as a dual sensor and, in particular, a detectional and positional sensor.

BACKGROUND

The field of medication delivery devices and systems includes "syringe pumps," which are typically pre-filled medication syringes mechanically driven under microprocessor control to deliver a prescribed dose of medication at a controlled rate to a patient through an infusion line fluidly connected to the syringe. A syringe pump typically includes a motor that rotates a leadscrew. The leadscrew in turn activates a plunger driver which forwardly pushes a plunger within a barrel of the syringe. Pushing the plunger forward thus forces the dose of medication outwardly from the syringe, into the infusion line, and to the patient intravenously or via any other suitable route. As used throughout this disclosure, the term "syringe pump" is intended to generally pertain to any medical device which acts on a syringe to controllably force fluid outwardly therefrom.

Typically in syringe pumps, a force sensor is positioned adjacent a syringe thumbpress in order to measure a force with which the pump is pushing on the syringe. This measured force can be used to determine fluid pressure inside the syringe which may be, for example, indicative of an undesirable downstream occlusion. While a force sensor adjacent the thumbpress is typically satisfactory for relatively large syringe pumps such as those that are provided near patient beds or otherwise employed in hospitals and clinical settings, it can be unsatisfactory or otherwise problematic for relatively small devices such as, for example, ambulatory syringe pumps wherein provision of a relatively compact device with an acceptable ingress protection rating may be of particular concern.

Attempts to address these problems or deficiencies have resulted in placing a force sensor internal to the pump to determine the fluid pressure. Another attempted approach is to place a force sensor in the moving plunger head and measure the syringe force directly. However, a separate sensor is then required to determine the correct placement or seating of the syringe thumbpress. One approach entails providing digital or analog thumbpress sensors as a component separate from the force sensor where the digital switch confirms that the thumbpress is in the correct position and the analog device measures the size of the thumbpress and verifies that it falls within the correct range. In addition, many syringe pumps further include a separate sensor that measures the linear position of the plunger head.

One problem with the above conventional approaches is that there exists relative motion between a main printed circuit board and the sensor, resulting in a moving electrical connection or moving wires between a component in motion (e.g., force sensor or thumbpress sensor) and a static component (e.g., main printed circuit board). Another problem is that numerous separate components must be provided which subsequently results in a more complex system.

Consequently, it would be useful and advantageous to provide systems and methods that solve the problems associated with syringe pumps as discussed above.

SUMMARY

The present disclosure relates to the detection and correct seating of the syringe thumbpress within the syringe pump and determination of the linear position of the plunger head in syringe pumps in a sensor system having relatively few moving parts and components. In particular, what is desired is a single sensor to detect that the syringe thumbpress is located or seated correctly (detectional sensor) and to determine the linear position of the plunger head (positional sensor).

Embodiments relate to methods, systems and devices for providing a combined detectional and positional sensor for a syringe pump that is relatively simple, inexpensive, and robust. The sensor can comprise a syringe thumbpress clamp that is pivotable so that an engagement pin deflects a linear membrane potentiometer first circuit, thus providing a closed switch for detection and a variable voltage or other signal return for indication of plunger head position.

BRIEF DESCRIPTION OF THE DRAWINGS

Embodiments disclosed herein may be more completely understood in consideration of the following detailed description of various example embodiments in connection with the accompanying drawings, in which:

FIG. 3a is a schematic diagram of a dual sensor as described herein, without a medication syringe in place, according to an embodiment.

FIG. 3b depicts a syringe thumbpress clamp, according to an embodiment.

FIG. 4a depicts a conventional membrane linear potentiometer, according to an embodiment.

FIG. 4b depicts a cross sectional view of a conventional membrane linear potentiometer when the engagement pin is activated, according to an embodiment.

Figure 1:
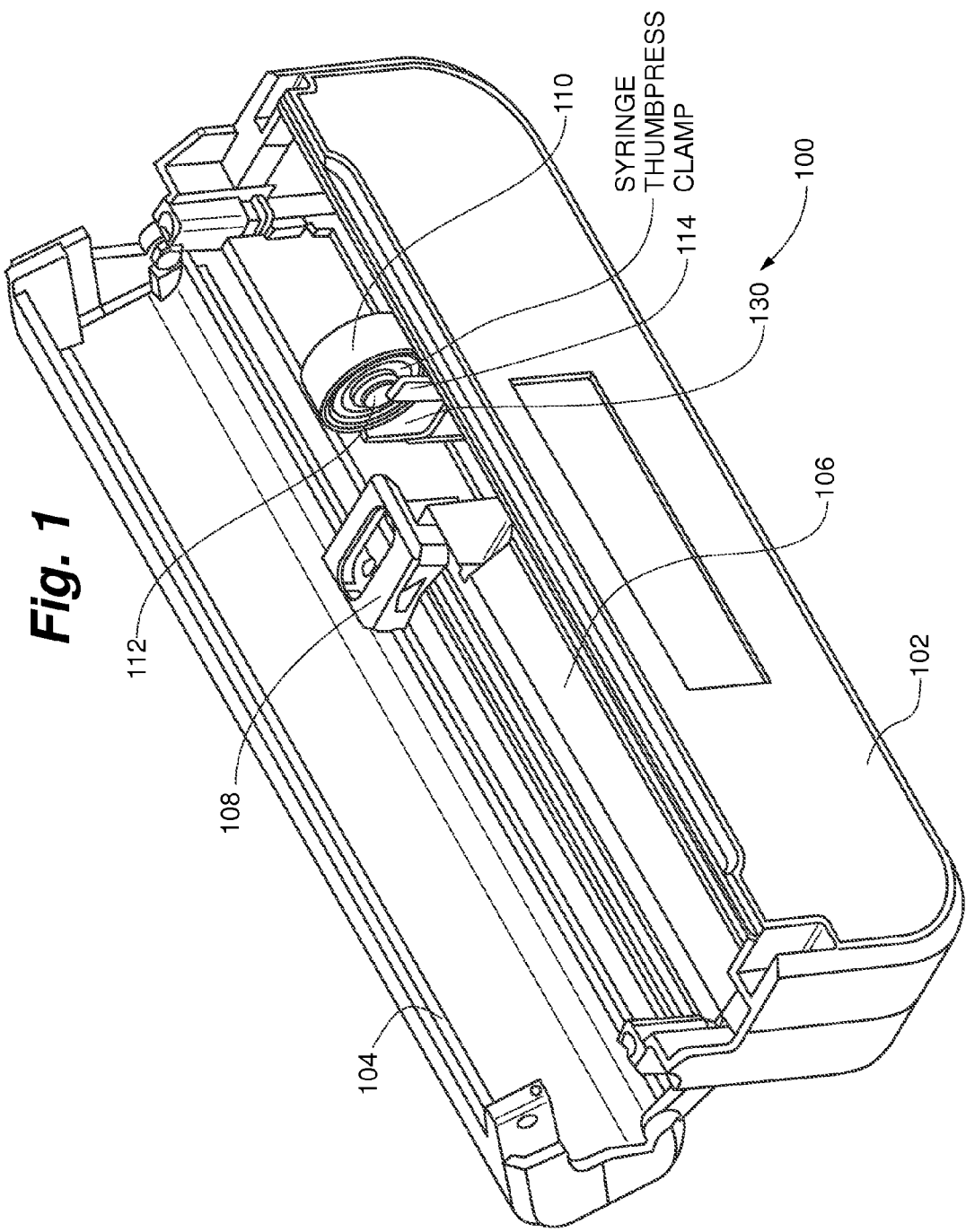
FIG. 1 illustrates an example embodiment of a relatively small, simple, and economical syringe pump.

While the subject matter hereof is amenable to various modifications and alternative forms, specifics thereof have been shown by way of example in the drawings and will be described in detail. It should be understood, however, that the intention is not to limit the subject matter hereof to the particular embodiments described. On the contrary, the intention is to cover all modifications, equivalents, and alternatives falling within the spirit and scope of the subject matter hereof.

DETAILED DESCRIPTION

Embodiments may be provided in other specific forms without departing from the essential attributes thereof. The illustrated embodiments should be considered in all respects as illustrative and not restrictive. The following detailed description should be read with reference to the drawings in which similar elements in different drawings are numbered similarly.

In various embodiments, devices, systems and methods are disclosed for a combination syringe thumbpress detection sensor and plunger head position sensor (detectional and positional sensor). Such a detectional and positional sensor ("sensor") is simple and robust while having fewer components and relatively few moving parts when compared with conventional devices and systems, thereby providing advantages over conventional syringe sensors. Embodiments of the sensor can be used in both relatively large syringe pumps (e.g., "hospital pumps") and in relatively small syringe pumps (e.g., "ambulatory pumps") and can take into account one or more of the ingress protection rating, force sensor accuracy and size requirements of the pump. In embodiments, the sensor comprises a single membrane linear potentiometer and syringe thumbpress clamp configured to act in concert to detect the presence and seating of the syringe thumbpress within the syringe pump and also to determine the linear position of the plunger head in syringe pumps. In an embodiment, the syringe thumbpress clamp is pivotable, transferring motion to an engagement pin that then deflects a linear membrane potentiometer first circuit. Deflecting the first circuit closes the switch for detection and provides a variable voltage or other signal return for indication of plunger head position. The sensor has relatively few moving parts and components.

Figure 2:
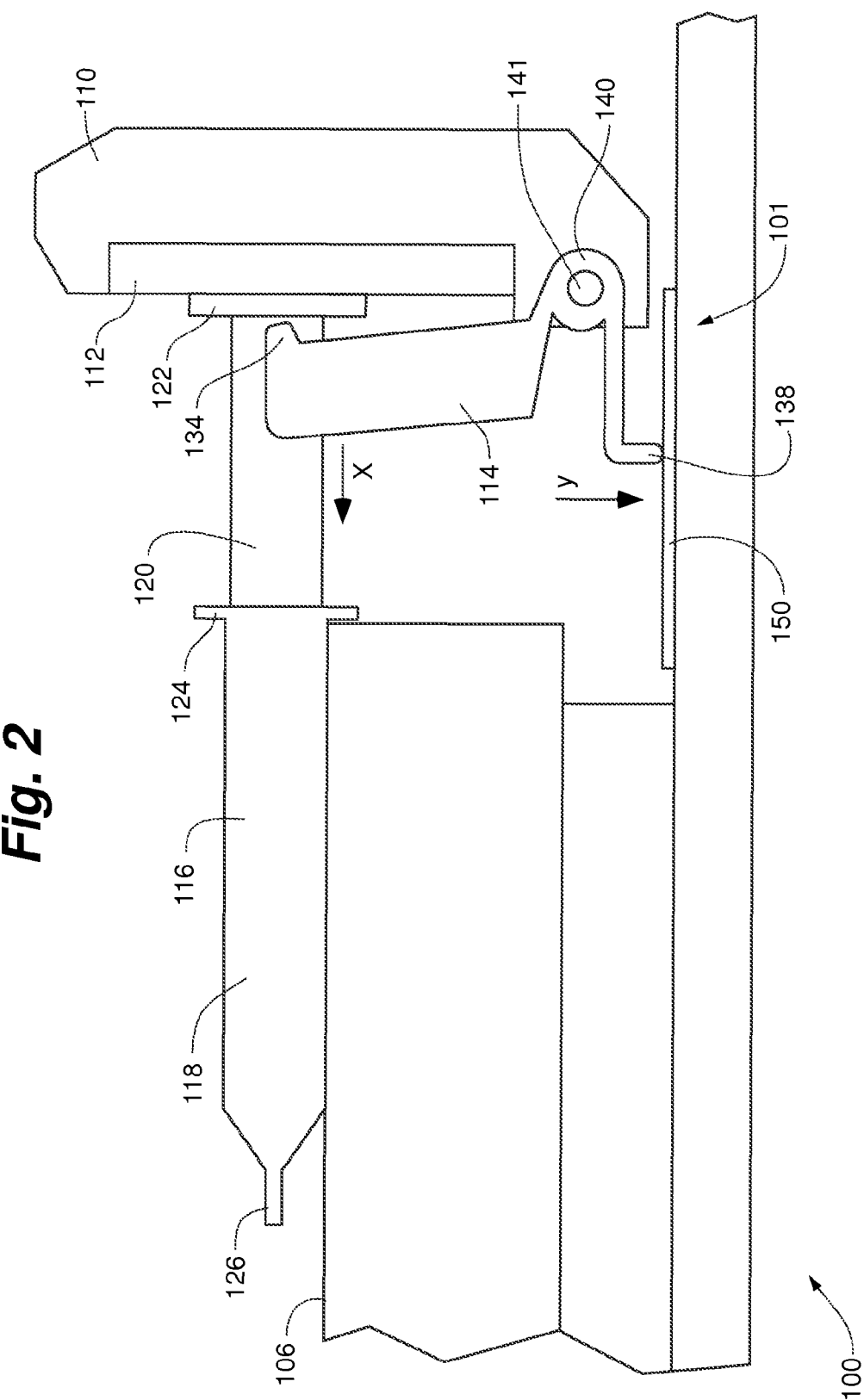
FIG. 2 is a schematic diagram of a syringe pump having a dual sensor as described herein, in use with a medication syringe, according to an embodiment.

FIG. 1 depicts an embodiment of an ambulatory or relatively small, simple, and economical syringe pump 100. Syringe pump 100 comprises an outer housing 102, a pivotable cover 104, a syringe barrel receiver 106, a syringe retaining clamp 108, a plunger driver 110, a force sensor 112, and a syringe thumbpress clamp 114, in the embodiment depicted. FIG. 2 schematically depicts a syringe 116 positioned in syringe pump 100. Syringe 116 comprises a barrel 118, a plunger 120, a thumbpress 122, a retaining component 124, and a tip 126, in an embodiment. Other embodiments of syringe pumps 100 and syringes 116 are contemplated as long as they are suitable for the purpose intended.

In an embodiment, a detectional and positional sensor 101 comprises two primary components, syringe thumbpress clamp 114 and a membrane linear potentiometer 150. Depicted in FIGS. 3a and 3b is one embodiment of syringe thumbpress clamp 114 comprising a body 130 configured as U-shaped, the U-shape dimensioned for receiving syringe plunger 120. In other embodiments, syringe thumbpress clamp 114 body 130 can be configured in shapes other than U-shaped, e.g., squared, V-shaped, semi-circular, semi-ovid, etc. Body 130 further comprises two arms 132, each arm 132 having a projection 134 on a distal end. Syringe thumbpress clamp 114 further comprises a pressure arm 136. A distal end of pressure arm 136 comprises a potentiometer engagement pin 138 and a proximal end of pressure arm 136 comprises a pivot ring 140. Pivot ring 140 can be fixedly attached to the bottom portion of the U-shaped body 130. It is contemplated that engagement pin 138 can be unitary with pressure arm 136 or be a separate component that is attached to pressure arm 136.

An embodiment of a membrane linear potentiometer 150 is depicted in FIGS. 4a and 4b. Potentiometer 150 comprises a first membrane surface 152 comprising a first circuit 154, a sealing layer 156, a second membrane surface 158 comprising a second circuit 160, and a base layer 162. In other embodiments, potentiometer 150 can be any configuration as is provided in the art so long as it operates in a similar or suitable manner. In an embodiment, base layer 162 bottom can be provided with an adhesive and potentiometer 150 can be adhered in syringe pump 100. In other embodiments, potentiometer 150 can be mounted with the use of screws or can be "snapped" in place or affixed in some other suitable way. In FIG. 4b, pin 138 has been additionally depicted, as will be further described in operation of potentiometer 150 and its first circuit 154.

FIG. 3a depicts an embodiment of the sensor 101 configuration in which syringe 116 is not positioned in syringe pump 100. As depicted in an embodiment, syringe thumbpress clamp 114 can be pivotably coupled to plunger driver 110 via pivot ring 140. Potentiometer engagement pin 138 can be positioned relative to first circuit 154 such that minimal contact (not shown) or no contact (shown) is made with first circuit 154. Projection 134 can be positioned adjacent driver 110 and can contact (not shown) driver 110 or maintain a gap (shown) between projection 134 and driver 110. In this configuration, linear membrane potentiometer 150 is an open circuit or a normally open switch thus sensing that syringe 116 is not positioned in syringe pump 100.

In operation, as shown in the embodiment depicted in FIG. 2, syringe 116 is inserted in syringe pump 100 so that barrel 118 is in contact with syringe barrel receiver 106. Plunger 120 is positioned in U-shaped portion of syringe thumbpress clamp 114 so that thumbpress 122 is placed between force sensor 112 and syringe thumbpress clamp 114. The presence of thumbpress 122 results in syringe thumbpress clamp 114 being moved in direction x causing syringe thumbpress clamp 114 to rotate about pivot point 141 which forces engagement pin 138 in direction y thus exerting force on first circuit 154. As shown in FIG. 4b, the force on first circuit 154 deflects first circuit 154 to make contact with second circuit 160, thus completing the circuit or closing the switch. Thus, presence detection of syringe 116 is accomplished due to linear membrane potentiometer 150 acting as a closed switch when the syringe 116 is present and an open switch when the syringe 116 is removed.

In addition, linear membrane potentiometer 150 is a dual sensor 101 further determining the linear position of the plunger head. When the switch is closed (i.e., syringe 116 is in place), a variable voltage or other signal is returned based upon the longitudinal position of engagement pin 138 in relation to potentiometer 150. Potentiometer 150 is a voltage divider generating a voltage output when the first circuit 154 makes contact with the second circuit 160. The voltage output is variable and changes as the engagement pin 138 moves longitudinally along the first circuit 154. Measuring the outputted voltage can give an indication of the linear position of the plunger head so that potentiometer 150 and syringe thumbpress clamp 114 provide a linear position function to sensor 101.

An advantage of embodiments is a single system that provides a dual sensor, detecting the presence of a syringe as well as the linear position of the plunger head, having relatively few components and moving parts. Another advantage of such a single, dual sensor system is that it does not involve motion or variable displacement between hard-wired components as aforementioned. It is also a simpler system than that of conventional systems known to those skilled in the art. And, due to relatively few components and moving parts, it can be more robust than conventional devices and systems.

Also as aforementioned, in embodiments the syringe thumbpress clamp is pivotable, transferring motion to an engagement pin that then deflects a linear membrane potentiometer first circuit. Deflecting the first circuit closes the switch for detection and provides a variable voltage return for indication of plunger head position. But it is to be appreciated and understood that other suitable components, devices, and techniques could be employed to provide such dual detection and position feedback including, e.g., laser interferometric and ultrasonic detection systems, provided that they function to (i) return no signal (or a first signal) when a syringe is not loaded and/or improperly loaded and (ii) return a signal (or a second signal, differentiated from the first signal) when a syringe is properly loaded, and then also provide an indication of linear displacement of the plunger. It is also to be understood that a normally open switch or circuit in a particular device could be replaced by a normally closed switch or circuit, provided that other related components are also replaced or adapted in a corresponding and suitable manner. For example, in an embodiment in which a normally open switch is replaced with a normally closed switch or circuit, a corresponding normally closed switch or circuit in the device is accordingly replaced by a normally open switch or circuit so that the two corresponding switches or circuits act opposite to each other in a particular embodiment as intended. It is further to be appreciated and understood that pivot ring 140 could be located either on thumbpress clamp 114 or on plunger driver 110, provided that pivot point 141 is located correspondingly with respect thereto.

While systems and devices for providing a combined detectional and positional sensor for a syringe pump have been particularly shown and described with reference to the accompanying figures and specification, it should be understood however that other modifications thereto are of course possible; and all of them are intended to be within the true spirit and scope of novel and inventive systems, devices and methods described herein. Thus, configurations and designs of various features could be modified or altered depending upon particular embodiments.

For example, in other embodiments, the following devices could be provided alone or in combination—and as alternatives or additions to the aforementioned single membrane linear potentiometer: (i) a dual membrane potentiometer-type device; (ii) a rigid potentiometer-type device wherein a "wiper" that makes contact across the potentiometer becomes electrically disengaged when a syringe is not present or improperly loaded in the pump; and (iii) any suitable potentiometer-type sensor that returns a "null" signal if there is no syringe present or if a syringe is incorrectly loaded and a variable voltage or other signal if the syringe is correctly loaded. It is to be appreciated and understood that in any of these example embodiments, a variable voltage or other signal—whether digital or analog—could then be proportional to and thus indicative of the position of the plunger head.

Although the combined detectional and positional sensor has been described by example with regard to relatively small syringe pumps such as ambulatory pumps and other relatively compact, simple, and economical syringe pumps, it is to be appreciated and understood that such a novel and inventive sensor could also be advantageously provided in relatively large, complex, and expensive pumps as well.

Additionally, dimensioning and scaling of the drawings herein have been chosen to clearly show details of example embodiments. Thus, in some embodiments it is possible that spacing between various features might be visually imperceptible—e.g., the syringe barrel and the barrel receiver. In any event, dimensioning and scaling could vary significantly across various embodiments of systems and devices for providing a combined detectional and positional sensor for a syringe pump.

It should also be appreciated that the exemplary embodiment or exemplary embodiments are only examples, and are not intended to limit the scope, applicability, or configuration of the subject matter hereof in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the subject matter hereof as set forth in the appended claims and the legal equivalents thereof.

The embodiments above are intended to be illustrative and not limiting. Additional embodiments are within the claims. Although the present subject matter has been described with reference to particular embodiments, those having skill in the art will recognize that changes may be made in form and detail without departing from the spirit and scope of the subject matter hereof.

Various modifications to the subject matter hereof may be apparent to one of skill in the art upon reading this disclosure. For example, persons of ordinary skill in the relevant art will recognize that the various features described for the different embodiments of the subject matter can be suitably combined, un-combined, and re-combined with other features, alone, or in different combinations, within the spirit of the subject matter hereof. Likewise, the various features described above should all be regarded as example embodiments, rather than limitations to the scope or spirit of the subject matter hereof. Therefore, the above is not contemplated to limit the scope of the present subject matter hereof.

For purposes of interpreting the claims for the present subject matter, it is expressly intended that the provisions of Section 112, sixth paragraph of 35 U.S.C. are not to be invoked unless the specific terms "means for" or "step for" are recited in a claim.

The invention claimed is:

1. A syringe pump sensor configured to detect a presence and seating of a syringe within a syringe pump (detection sensing) and a linear position of a plunger head of the syringe (positional sensing), the syringe pump sensor comprising:
   a syringe thumbpress clamp; and
   a linear membrane potentiometer coupled to the syringe thumbpress clamp,
   wherein the thumbpress clamp includes a first arm having a projection configured to engage with the syringe, a second arm having a potentiometer engagement pin configured to engage with the linear membrane potentiometer, and a pivot ring, with the first arm, the second arm and the pivot ring comprising a unitary, substantially rigid component.

2. The syringe pump detectional and positional sensor of claim 1, wherein the linear membrane potentiometer has a first circuit and a second circuit, wherein the first circuit is deflectable.

3. A syringe pump detectional and positional sensor comprising:
   a syringe thumbpress clamp comprising a first arm having a projection on a distal end of the arm, a pivot ring, and a pressure arm having an engagement pin at a distal end of the pressure arm, wherein the first arm, the pivot ring and the second arm comprise a unitary, substantially rigid component; and a linear membrane potentiometer comprising a first circuit and a second circuit, wherein the first circuit is deflectable.

4. A syringe pump sensor configured to detect a proper seating of a syringe within a syringe pump and a linear position of a plunger head of the syringe, the syringe pump sensor comprising:

a unitary, substantially rigid holder having a first arm configured to engage with a portion of the syringe, a second arm having an engagement pin and a pivot ring positioned therebetween;

a switch in contact with the engagement pin; and a variable signal indicator in movable contact with the engagement pin.

* * * * *